(12) United States Patent
Moon et al.

(10) Patent No.: US 9,828,402 B2
(45) Date of Patent: Nov. 28, 2017

(54) FILM-FORMING COMPOSITION AND METHOD FOR FABRICATING FILM BY USING THE SAME

(71) Applicants: SK hynix Inc., Gyeonggi-do (KR); SOULBRAIN SIGMA-ALDRICH, LTD, Chungcheongnam-do (KR)

(72) Inventors: Ji-Won Moon, Gyeonggi-do (KR); Young-Jin Son, Gyeonggi-do (KR); Jeong-Yeop Lee, Gyeonggi-do (KR); Jun-Soo Jang, Gyeonggi-do (KR); Jae-Sun Jung, Chungcheongnam-do (KR); Sang-Kyung Lee, Chungcheongnam-do (KR); Chang-Sung Hong, Chungcheongnam-do (KR); Hyun-Joon Kim, Chungcheongnam-do (KR); Jin-Ho Shin, Chungcheongnam-do (KR); Dae-Hyun Kim, Chungcheongnam-do (KR)

(73) Assignees: SK Hynix Inc., Gyeonggi-do (KR); SOULBRAIN SIGMA-ALDRICH, LTD, Chungcheongnam-do (KR)

( * ) Notice: Subject to any disclaimer, the term of this patent is extended or adjusted under 35 U.S.C. 154(b) by 0 days.

(21) Appl. No.: 14/855,697

(22) Filed: Sep. 16, 2015

(65) Prior Publication Data
US 2016/0273103 A1   Sep. 22, 2016

(30) Foreign Application Priority Data
Mar. 20, 2015 (KR) .......... 10-2015-0039112

(51) Int. Cl.
| C23C 16/18 | (2006.01) |
|---|---|
| C07F 17/00 | (2006.01) |
| C07F 7/00 | (2006.01) |
| C23C 16/40 | (2006.01) |
| C23C 16/455 | (2006.01) |

(52) U.S. Cl.
CPC .............. *C07F 17/00* (2013.01); *C07F 7/006* (2013.01); *C23C 16/18* (2013.01); *C23C 16/405* (2013.01); *C23C 16/45553* (2013.01)

(58) Field of Classification Search
CPC .... C23C 16/18; C23C 16/45525; C23C 16/06
USPC ........................................................ 427/248.1
See application file for complete search history.

(56) References Cited

U.S. PATENT DOCUMENTS

| 5,900,279 | A | * | 5/1999 | Hideaki | .................. C23C 16/18 |
|---|---|---|---|---|---|
| | | | | | 427/229 |
| 6,984,591 | B1 | | 1/2006 | Buchanan et al. | |
| 7,998,883 | B2 | | 8/2011 | Putkonen | |
| 8,420,864 | B2 | | 4/2013 | Ruppin et al. | |
| 2008/0254218 | A1 | | 10/2008 | Lei et al. | |
| 2010/0112211 | A1 | | 5/2010 | Xu et al. | |

(Continued)

FOREIGN PATENT DOCUMENTS

| KR | 1020120105070 | 9/2012 |
|---|---|---|
| KR | 1020140078534 | 6/2014 |

*Primary Examiner* — Elizabeth Burkhart
(74) *Attorney, Agent, or Firm* — IP & T Group LLP

(57) ABSTRACT

A film-forming composition including a 3-intracyclic cyclopentadienyl precursor and dimethyethylamine is useful for Atomic Layer Deposition, and improves viscosity and volatility while maintaining unique features of metal precursors.

12 Claims, 5 Drawing Sheets

(56) References Cited

U.S. PATENT DOCUMENTS

2010/0270508 A1 10/2010 Xu et al.
2013/0337659 A1* 12/2013 Ahn ..................... C23C 16/18
                                                        438/785

* cited by examiner

FILM-FORMING COMPOSITION AND METHOD FOR FABRICATING FILM BY USING THE SAME

CROSS-REFERENCE TO RELATED APPLICATIONS

The present application claims priority of Korean Patent Application No. 10-2015-0039112, filed on Mar. 20, 2015, which is herein incorporated by reference in its entirety.

BACKGROUND

1. Field

Exemplary embodiments of the present invention relate to a film-forming composition.

2. Description of the Related Art

There are several constraints on materials which are used as a film-forming composition, for example, by atomic layer deposition using liquid delivery system (LDS). Solid materials are not properly used as the film-forming composition. Liquid materials with high viscosity may not be evenly dispersed in a chamber so that uniformity and step coverage of a film become reduced.

SUMMARY

An exemplary embodiment of the present invention is directed to a film-forming composition that may improve viscosity and volatility while maintaining unique features of metal precursors.

Another exemplary embodiment of the present invention is directed to a method for fabricating a film by using the film-forming composition.

In accordance with an embodiment of the present invention, a film-forming composition includes a precursor and dimethyethylamine, wherein the precursor is represented by the following formula 1:

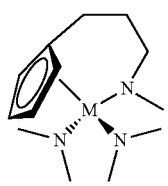

[Formula 1]

wherein M may be selected from the group consisting of Zr, Hf and Ti. The dimethyethylamine may included in the composition in an amount of 1 to 99 wt % based on the total amount of the composition. The precursor and the dimethyethylamine have a weight ratio of 1:99 to 99:1.

In accordance with an embodiment of the present invention, a method for fabricating a film may includes depositing a film on a substrate by using a film-forming composition, wherein the film-forming composition may including a precursor and dimethylethylamine, wherein the precursor is represented by the following formula 1:

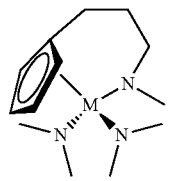

[Formula 1]

wherein M is selected from the group consisting of Zr, Hf and Ti. The film is deposited by Atomic Layer Deposition. The depositing of the film includes: preparing a liquid-phase composition by dissolving the precursor in the dimethyethylamine, placing a substrate in a chamber, and introducing the liquid-phase composition into the chamber through Liquid Delivery System. The depositing of the film may further includes vaporizing the liquid-phase composition, and wherein the Introducing of the liquid-phase composition includes introducing the vaporized liquid-phase composition into the chamber. The dimethyethylamine may included in an amount of 1 to 99 wt % based on the total amount of the film-forming composition. The precursor and the dimethyethylamine has a weight ratio of 1:99 to 99:1.

In accordance with another embodiment of the present invention, a film-forming composition includes a precursor and dimethylethylamine, wherein the precursor is represented by the following Formula 2:

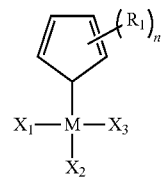

[Formula 2]

wherein M is selected from the group consisting of Zr, Ti and Hf, R1 is independently hydrogen or $C_1$-$C_4$ alkyl, n is independently an integer of 0, 1, 2, 3, 4 or 5, $X_1$, $X_2$ and $X_3$ are independently —$NR_2R_3$ or —$OR_4$, wherein $R_2$, $R_3$ and $R_4$ independently include $C_1$-$C_6$ alkyl.

In accordance with yet another embodiment of the present invention, a film-forming composition includes a precursor and dimethylethylamine, wherein the precursor is represented by the following Formula 3:

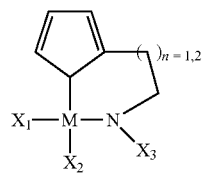

[Formula 3]

wherein M is selected from the group consisting of Zr, Ti and Hf, $X_1$, $X_2$ and $X_3$ are independently —$NR_1R_2$ or —$OR_3$, wherein $R_1$, $R_2$ and $R_3$ independently include $C_1$-$C_6$ alkyl, wherein n is 1 or 2.

The dimethylethylamine may have a boiling point of 70° C. or less, a density at 25° C. of 0.6 to 0.8 g/cm³, and a vapor pressure of 400 to 700 mmHg.

In accordance with yet another embodiment of the present invention, a film-forming composition includes a liquid-phase precursor by dissolving a metal precursor in dimethyethylamine, wherein the metal precursor includes a propylamino group and a cyclopentadienyl group. The metal precursor has a structure of formula 1:

[Formula 1]

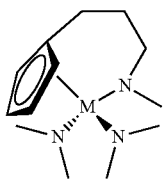

wherein M is selected from the group consisting of Zr, Hf and Ti. The dimethyethylamine may included in the composition in an amount of 1 to 99 wt % based on the total amount of the composition. The metal precursor and the dimethyethylamine has a weight ratio of 1:99 to 99:1.

In accordance with still yet another embodiment of the present invention, a method for fabricating a film may includes preparing a liquid-phase metal precursor by dissolving a metal precursor dimethyethylamine, wherein the metal precursor may include a cyclopentadienyl group and propylamino group; vaporizing the liquid-phase metal precursor and introducing the vaporized metal precursor into a chamber with a substrate; adsorbing the vaporized metal precursor on the substrate; feeding a reactant reactable with the adsorbed metal precursor into the chamber in order to deposit a metal-containing film on the substrate. The metal precursor is represented by the following formula 1:

[Formula 1]

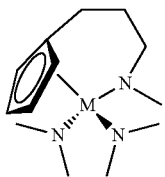

wherein M is selected from the group consisting of Zr, Hf and Ti. The metal-containing film may include a metal selected from the group consisting of Zr, Ti, Hf, an oxide of the metal, and a nitride of the metal. The depositing of the metal-containing film is performed by atomic layer deposition or chemical vapor deposition.

DETAILED DESCRIPTION

Figure 1:
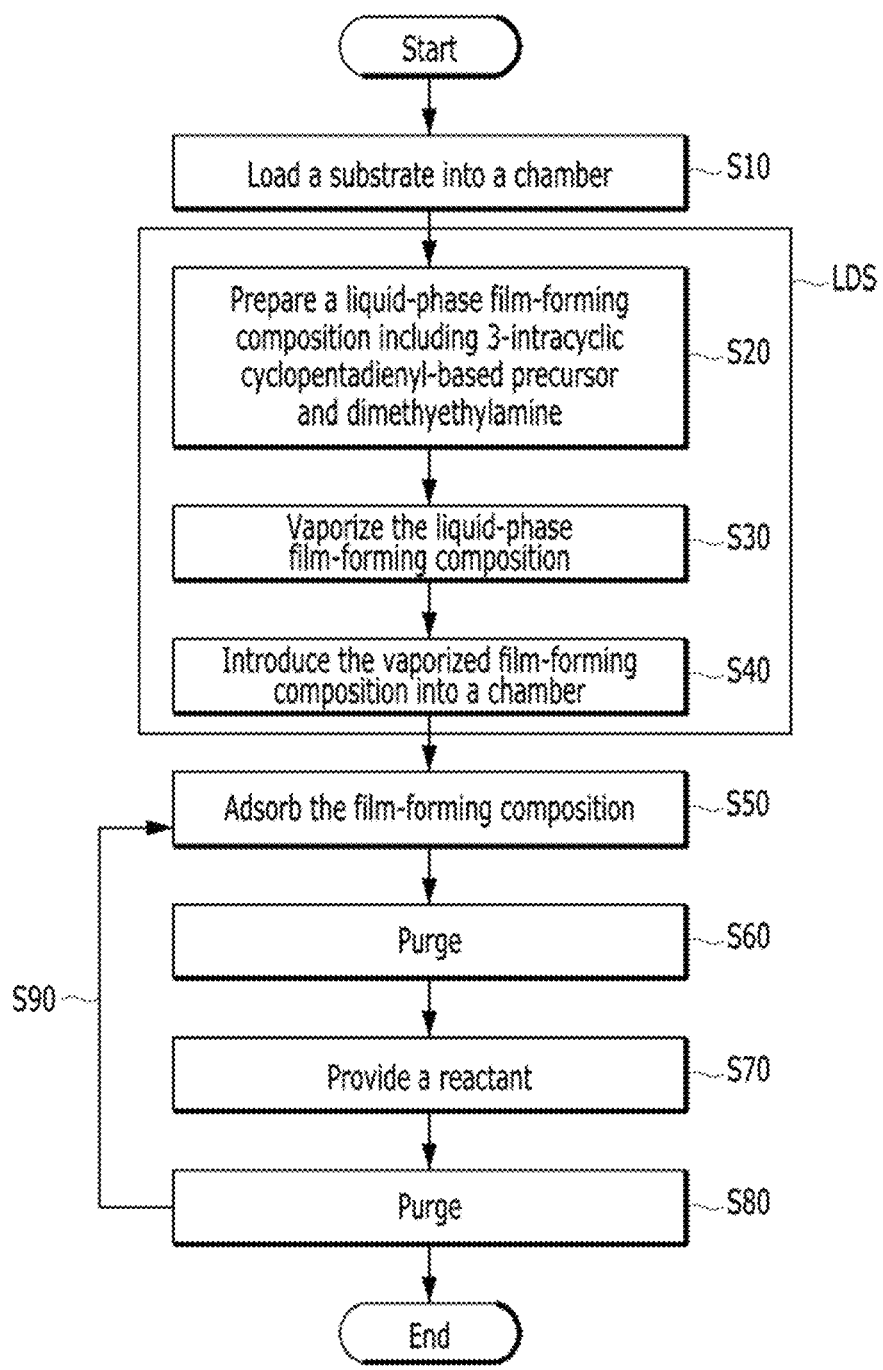
FIG. 1 is a view illustrating a method for fabricating a film in accordance with an embodiment of the present invention.

Exemplary embodiments of the present invention will be described below in more detail with reference to the accompanying drawings. The present invention, however, should not be construed as limited to the embodiments set forth herein. Throughout the disclosure, like reference numerals refer to like parts throughout the various figures and embodiments of the present invention.

The drawings are not necessarily to scale and in some instances, proportions may have been exaggerated to clearly illustrate features of the embodiments. When a first layer is referred to as being "on" a second layer or "on" a substrate, it not only refers to a case where the first layer is formed directly on the second layer or the substrate but also a case where a third layer exists between the first layer and the second layer or the substrate.

Standard chemical symbols in the periodic table are used herein in order to describe exemplary embodiments of the present invention. Elements may be expressed as the standard chemical symbols, for example, Ti, Hf and Zr mean titanium, hafnium and zirconium, respectively.

As described herein, the term "independently" in the context of a substituent R means that the corresponding substituent R may be selected independently from other substituent R having the same or different subscript or superscript. Also, the corresponding substituent R may be selected independently from any substituent R having the same subscript or superscript. Unless otherwise described, it should be understood that a substituent R in one chemical formula is selected independently from a substituent R in another chemical formula.

As described herein, the term "alkyl" means a saturated functional group exclusively containing carbon atoms and hydrogen atoms. Also, the term "alkyl" includes a straight, branched, or cyclic alkyl group. Examples of the straight alkyl group include, but are not limited to, methyl, ethyl, propyl, and butyl groups.

Herein, the term "Me" and "Cp" may mean methyl and cyclopentadienyl groups, respectively.

Precursor

In accordance with exemplary embodiments of the present invention, a precursor may be a material containing a metal (M). The metal (M) is contained in a film which is formed on a substrate. In an embodiment, the metal may include elements of group IIA, IIIB, IVB or VB. For examples, the metal may include, but are not limited to, Be, Mg, Ca, Sr, Ba, Ra, Sc, Y, La, Ac, Ce, Th, Ti, Zr, Hf, Rf, Pr, Pa, V, Nb, Ta, Db, Nd or U. In another embodiment, in addition to the above metal elements, any metal element in the periodic table can be used. Hereinafter, in exemplary embodiments, the metal (M) may include zirconium (Zr), hafnium (Hf), or titanium (Ti).

The precursor may include an organic metal precursor. In this embodiment, the precursor may include compounds having thermal stability and high viscosity. For example, the precursor may include "3-intracyclic cyclopentadienyl (3-intracyclic Cp)" precursor. The 3-intracyclic cyclopentadienyl precursor is an asymmetric-compound containing a cyclopentadienyl group (Cp) forming an intracyclic ring. Such 3-intracyclic cyclopentadienyl precursor has thermal stability due to an appropriate distribution (physical properties and thermal stability at distribution temperature) and a broad range of self-limiting ALD. For example, the 3-intracyclic cyclopentadienyl precursor has higher thermal stability than that of teterkis(ehtylmethylamino)zirconium (TEMAZr), cyclopentadienyltris(dimethylamido)zirconium (CpZr(NMe$_2$)$_3$) or Cp(CH$_2$)$_2$NMeZr(NMe$_2$)$_2$. As such, the 3-intracyclic cyclopentadienyl precursor is thermally more stable than a cyclopentadienyl (Cp)-Zr precursor and a 2-intracyclic cyclopentadienyl (2-intracyclic Cp)-Zr precursor.

To improve thermal stability, a conventional precursor including Cp-Zr—N—CH$_3$ may be modified to form a cyclic bond between Cp and N and obtain the 3-intracyclic cyclopentadienyl zirconium (3-intracyclic Cp-Zr) precursor to be thermally decomposed at a relatively high temperature.

To improve not only thermal stability but also viscosity, it is necessary to use a precursor material including the 3-intracyclic cyclopentadienyl zirconium precursor and a Gas Phase Stabilizer (GPS). However, such a precursor material has high viscosity (>10 Cp) and it is difficult to apply a Liquid Delivery System (LDS) for mass production. Moreover, the precursor material may be used only with a deposition method using a vapor pressure at a high temperature. Particle issues may be raised to reduce the vaporization efficiency and it is difficult to apply the precursor material to DRAM.

For example, a precursor such as Cp(CH$_2$)$_3$NMeZr (NMe$_2$)$_2$ (wherein, Cp=cyclopentadienyl, Me=methyl, DMA=dimethylamino), is difficult to be sufficiently vaporized in a vaporizer of the Liquid Delivery System (LDS) due to high viscosity. As a result, a process pressure is not sufficiently high so that the precursor may not be evenly delivered on a substrate and results in poor distribution on the substrate. On the contrary, in accordance with exemplary embodiments of the present invention, the precursor is diluted with a solvent so that viscosity and distribution characteristics may be improved, and thus the obtained film has enhanced uniformity and step coverage properties.

In an embodiment, it is necessary to add a specific Gas Phase Stabilizer (GPS) to the 3-intracyclic cyclopentadienyl zirconium precursor. Preferably, the specific Gas Phase Stabilizer (GPS) does not cause an additional reaction and may be selected in consideration of thermal properties such as heat capacity (HC). Moreover, in a process of synthesizing a precursor, a conventional solid precursor is converted into a liquid precursor and the viscosity of the liquid precursor is lower than 10 Cp and adjustable as desired.

That is, a film-forming composition in accordance with an embodiment may include, as a solute, 3-intracyclic cyclopentadienyl precursor of formula 1:

[Formula 1]

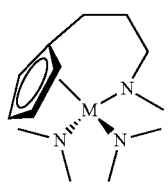

wherein M may be Zr, Hf, or Ti. The film-forming composition contains dimethylethylamine (DMEA) as a solvent.

Specifically, the precursor of formula 1 may include (methyl-3-cyclopentadienylpropylamino)bis(dimethylamino)zirconium (Cp(CH$_2$)$_3$NMeZr(NMe$_2$)$_2$), (methyl-3-cyclopentadienylpropylamino)bis(dimethylamino)hafnium (Cp(CH$_2$)$_3$NMeHf(NMe$_2$)$_2$) or (methyl-3-cyclopentadienyl-propylamino)bis(dimethylamino)titanium (Cp(CH$_2$)$_3$NMeTi(NMe$_2$)$_2$).

The precursor of formula 1 has excellent thermal stability so that a film may be formed with improved film properties, for example, through an ALD process.

The precursor of formula 1 is in liquid phase. In this context, in accordance with an exemplary embodiment of the present invention, a tertiary amine having excellent miscibility with the precursor of formula 1 may be used as a solvent.

Specifically, the tertiary amine may have a boiling point of 70° C. or less, or 30 to 50° C., a density of 0.6 to 0.8 g/cm$^3$ at 25° C., and a vapor pressure of 400 to 700 mmHg. When the above requirement for the boiling point, the density and the vapor pressure are simultaneously fulfilled, viscosity significantly reduces and volatility of the film-forming composition significantly improves. As a result, a film can be formed with improved uniformity and step coverage.

Tertiary amine may meet the above conditions. That is, tertiary amine has a boiling point of 30 to 50° C., a density at temperature 25° C. of 0.65 to 0.77 g/cm$^3$, and a vapor pressure of 450 to 600 mmHg.

More specifically, the tertiary amine may be dimethyethylamine (DMEA). The tertiary amine may be included in a ratio of 1 to 99 wt % based on the total weight of the film-forming composition. If the amount of the tertiary amine is less than 1 wt %, the improvement effect on film properties may not be significant. If the amount of the tertiary amine is more than 99 wt %, the precursor concentration is too low and the improvement effect on step coverage properties may be reduced.

More specifically, the film-forming composition may preferably have the precursor and the tertiary amine in a weight ratio of 90:10 to 10:90. If the amount of the tertiary amine to the precursor is outside of the range, the improvement effect on uniformity and step coverage may be reduced.

As such, use of the tertiary amine having low viscosity and high volatility along with a proper solvent improves viscosity and volatility properties of the film-forming composition.

Accordingly, adsorption efficiency and stability of the precursor may be increased and process time may be reduced. Moreover, since the precursor is diluted with a solvent and then vaporized, it may be uniformly introduced into the chamber and evenly adsorbed on the substrate. As a result, it is possible to significantly enhance uniformity and step coverage of the deposited film. In addition, surplus non-covalent electron pairs of the tertiary amine may increase stability during adsorption of the precursor on the substrate so that chemical vapor deposition (CVD) reaction may be suppressed during ALD process.

As described above, metal films may be formed by using the film-forming composition including the 3-intracyclic cyclopentadienyl precursor stabilized with the tertiary amine. In addition, a metal oxide film and a metal nitride film may be formed by further providing the film-forming composition with a oxygen or nitrogen source, respectively.

Examples of deposition methods useful to form these films may include, but are not limited to, Metal Organic Chemical Vapor Deposition (MOCVD) or evaporation in addition to Atomic Layer Deposition (ALD).

The precursor of formula 1 has an asymmetric-structure. In this context, the asymmetric-structure may be referred to as a structure having a central metal coupled to different ligands from each other, for example, Cp and DMEA. In contrary, a symmetric structure may be referred to as a structure having a central metal coupled to four same ligands as each other. For example, TEMAZr has a symmetrical structure having a Zr metal coupled to four EMA ligands.

A film-forming composition in accordance with another embodiment may include an asymmetric precursor including a cyclopentadienyl group and dimethyethylamine.

A film-forming composition in accordance with yet another embodiment may include an asymmetric precursor including a cyclopentadienyl group and dimethyethylamine, wherein the cyclopentadienyl group has at least 2-intracyclic ring. For example, the precursor including a cyclopentadienyl group having 2- or 4-intracyclic ring (2-intracyclic or 4-intracyclic) other than 3-intracyclic ring may be used. 2-intra-cyclic Cp precursor including Cp and DMEA may be referred to as a linked amido-Cp complex. For example, 2-Intracyclic Cp and 3-intracyclic Cp may be referred to as ethyl linkage Cp and propyl linkage Cp, respectively.

A film-forming composition in accordance with yet another embodiment may include a cyclopentadienyl-based precursor of formula 2 and dimethylethylamine (DMEA). Dimethylethylamine (DMEA) serves as a solvent.

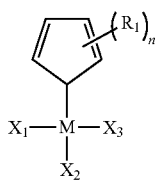

[Formula 2]

M may be Zr, Ti, or Hf. R1 is independently hydrogen or $C_1$-$C_4$ alkyl. n is independently an integer of 0, 1, 2, 3, 4 or 5. $X_1$, $X_2$ and $X_3$ are independently —$NR_2R_3$ or —$OR_4$. $R_2$, $R_3$ and $R_4$ may independently include $C_1$-$C_6$ alkyl.

A film-forming composition in accordance with still yet another embodiment may include a cyclopentadienyl-based precursor of formula 3 and dimethylethylamine (DMEA). Dimethylethylamine (DMEA) serves as a solvent.

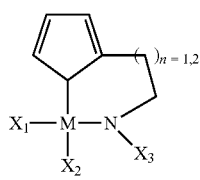

[Formula 3]

M may be Zr, Ti, or Hf. $X_1$, $X_2$ and $X_3$ are independently —$NR_1R_2$ or —$OR_3$. $R_1$, $R_2$ and $R_3$ may independently include $C_1$-$C_6$ alkyl. n is 1 or 2. For example, when n=1, then ethylene exists between Cp and N. When n=2, then propylene exists between Cp and N.

FIG. 1 is a view illustrating a method for fabricating a film in accordance with an embodiment of the present invention.

Referring to FIG. 1, a substrate on which a film is to be formed is placed in a chamber (S10). The substrate may include a silicon substrate, a silicon germanium substrate or a Silicon On Insulator (SOI) substrate. A conducting layer or an insulating layer may be further formed on the substrate. Atomic Layer Deposition (ALD) or Chemical Vapor Deposition (CVD) may be performed in the chamber. This embodiment will be described with respect to the Atomic Layer Deposition (ALD).

A film-forming composition is prepared (S20). The film-forming composition may include a precursor that is stabilized with tertiary amine. The precursor may include a compound of any one of formulae 1 to 3. The film-forming composition may be a liquid including a 3-intracyclic cyclopentadienyl-based precursor and dimethyethylamine. For example, the film-forming composition may be a liquid-phase metal precursor including a precursor and dimethyethylamine(DMEA). The precursor may include any one metal of Zr, Ti, and Hf.

The liquid-phase film-forming composition is vaporized (S30). The liquid-phase film-forming composition is fed into a vaporizer to form a vapor phase and then introduced into the chamber.

The vaporized film-forming composition is introduced into the chamber (S40). Examples of methods for introducing the precursor may include, but not limited to, delivering the composition in a gas state at such a pressure which is the same as or higher than its vapor pressure, Direct Liquid Injection or Liquid Delivery System (LDS). In LDS, the precursor is dissolved in an organic solvent and introduced into the chamber.

As described above, in accordance with this embodiment, Liquid Delivery System (LDS) including liquid-phase film-forming composition preparing step (S20), vaporizing step (S30) and introducing step (S40) may be applied to deliver the liquid-phase film-forming composition to the chamber. A carrier gas or a dilution gas for transporting the precursor to the substrate may include one or more inert gases selected from Ar, $N_2$, He or $H_2$.

Under this condition, the introduced film-forming composition is adsorbed on the substrate (S50).

Subsequently, the unabsorbed film-forming composition is purged (S60). An inert gas may be used as a purge gas.

Then, a reactant is provided (S70). The reactant may include an oxidizing agent such as $H_2O$, $H_2O_2$, $O_2$, $O_3$ or $N_2O$. For example, the reactant reacts with the adsorbed film-forming composition to form a metal oxide film. The metal oxide film may include zirconium oxide, titanium oxide or hafnium oxide.

Subsequently, the unreacted reactant is purged (S80). Accordingly, an excess reactant and a by-product may be removed.

The adsorbing step, purge, reactant-providing step and purge constitute a unit-cycle. The unit-cycle may be repeated until a film having a desired thickness is obtained (S90). For example, the unit-cycle may be repeated 10 to 10000 times.

When the metal oxide film is deposited on the substrate, the deposition temperature may be 250 to 400° C.

In another embodiment, the reactant may include a reducing agent such as $NH_3$ or a nitriding agent such as $N_2$ other than the oxidizing agent. A metal film and a metal nitride film may be deposited by using the reducing agent and the nitriding agent, respectively. In addition, a plasma of the reactant may be used as the reactant. Examples of the plasma may include RF plasma, DC plasma and Remote plasma. For example, use of the nitriding agent may result in deposition of a zirconium nitride film.

In another embodiment, the precursor may be heated at 20-200° C. to introduce it into the chamber.

In another embodiment, the reactant is diluted with an inert gas and then provided into the reactor to react with the precursor for 1 ms to 1 min.

To deposit the film as above, conventional atomic layer deposition may be performed.

In consideration of the properties of the film-forming composition and the improvement effect on the properties of the resultant film, atomic layer deposition in type of LDS as described in FIG. 1 may be more preferred. Moreover, it is possible to variously adjust the properties and composition of the resultant film by controlling conditions for the deposition.

Figure 2:
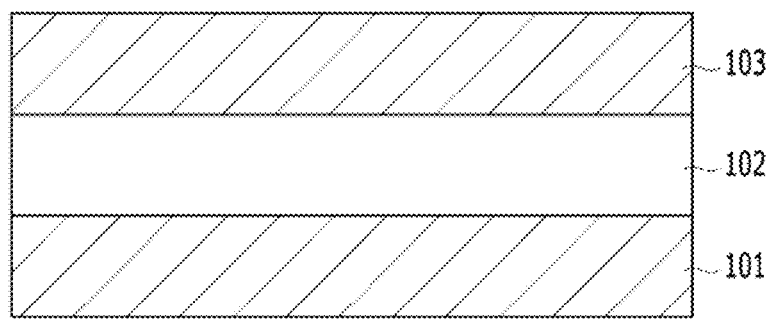
FIG. 2 is a view illustrating a capacitor formed using a method for fabricating a film in accordance with an embodiment of the present invention.

FIG. 2 is a view illustrating a capacitor formed using a method for fabricating a film in accordance with an embodiment of the present invention.

Referring to FIG. 2, the capacitor may include a bottom electrode 101, a dielectric layer 102 and a top electrode 103. The bottom electrode 101 and the top electrode 103 may include metal materials. In one embodiment, the bottom electrode 101 may have a plate shape. In another embodiment, the bottom electrode 101 may have a cylinder or a pillar shape.

The dielectric layer 102 may include a metal oxide film that is deposited by using the above film-forming composition. For example, the dielectric layer 102 may include zirconium oxide, titanium oxide or hafnium oxide. In another embodiment, the dielectric layer 102 may be formed of a stack or a mixture of at least two oxide films selected from zirconium oxide, titanium oxide and hafnium oxide.

When the dielectric layer 102 is deposited on the cylinder- or pillar-shaped bottom electrode 101 according to the above method, step coverage of the dielectric layer 102 may be improved.

Figure 3:
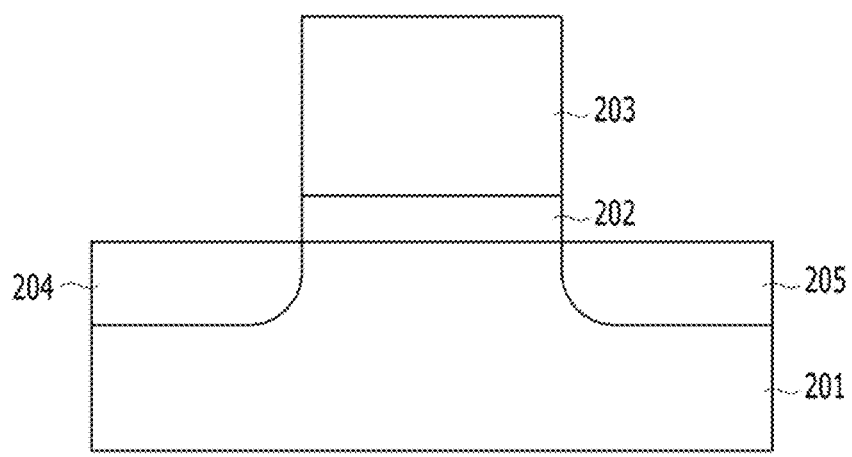
FIG. 3 is a view illustrating a transistor formed using a method for fabricating a film in accordance with an embodiment of the present invention.

FIG. 3 is a view illustrating a transistor formed using a method for fabricating a film in accordance with an embodiment of the present invention.

Referring to FIG. 3, the transistor is formed on a substrate 201 and may include a gate insulation layer 202, a gate electrode 203, a source region 204 and a drain region 205. The gate electrode 203 may include metal materials.

The gate insulation layer 202 may include a metal oxide film deposited by using the above film-forming composition. For example, the gate insulation layer 202 may include zirconium oxide, titanium oxide or hafnium oxide. In another embodiment, the gate insulation layer 202 may be formed of a stack or a mixture of at least two oxide films selected from zirconium oxide, titanium oxide and hafnium oxide.

According to the above embodiment, the film may be deposited at a higher temperature in comparison with conventional precursors by using the film-forming composition including the 3-intracyclic cyclopentadienyl precursor and dimethyethylamine (DMEA). Moreover, since a process employing the film-forming composition in accordance with the embodiment can be performed at a broader range of temperatures in comparison with conventional precursors, a film with improved crystallinity can be formed. Thus, the film with a given thickness may have relatively higher dielectric characteristics than a conventional film.

The film-forming composition in accordance with the embodiment may increase thermal stability in gas phases and enhance surface reactions to improve step coverage even in a case of a high aspect ratio.

Experimental Embodiment: Preparing a Film-Forming Composition and Forming a Film $Cp(CH_2)_3NMeZr(NMe_2)_2$ was dissolved in DMEA to prepare a film-forming composition. The amount of DMEA was 20 wt % based on the total weight of the composition. The composition was contained in a bubbler and fed into a vaporizer using a Liquid Mass Flow Controller (LMFC). Argon gas is provided at 100 sccm in room temperature. The vaporizer was heated to 150° C. at a rate of 0.05 g/min. A vapor-phase composition was formed in the vaporizer and then the vapor-phase composition was introduced into the chamber for 5 seconds. Then, argon purging was performed by providing the chamber with argon gas at 100 sccm for 10 seconds. Here, pressure in the chamber was controlled to 1 Torr. Next, ozone ($O_3$) was introduced into the chamber for 5 seconds and then argon purging was performed for 10 seconds. A substrate on which a metal film is to be formed was heated to 300° C. Such a process was repeated 200 times to obtain a ZrO film which is a self-limiting atomic layer.

Test for the Improvement Effect on Viscosity Properties

Viscosity of $Cp(CH_2)_3NMeZr(NMe_2)_2$ at room temperature is 25.4 $MPa^{-S}$ which is about 3 times higher than that of $CpZr(DMA)_3$, 8.2 $MPa^{-S}$. To compare viscosity of $Cp(CH_2)_3NMeZr(NMe_2)_2$ which is diluted with a solvent and viscosity of $Cp(CH_2)_3NMeZr(NMe_2)_2$ which is not diluted with a solvent, $Cp(CH_2)_3NMeZr(NMe_2)_2$ was dissolved into various solvents.

Saturated hydrocarbon such as pentane, unsaturated hydrocarbon such as toluene, and tertiary amine such as dimethyethylamine (DMEA) and N-methylpyrrolidine were used as the dilution solvents. A dilution ratio of $Cp(CH_2)_3NMeZr(NMe_2)_2$ was measured by wt %. The results are shown in FIG. 4.

Figure 4:
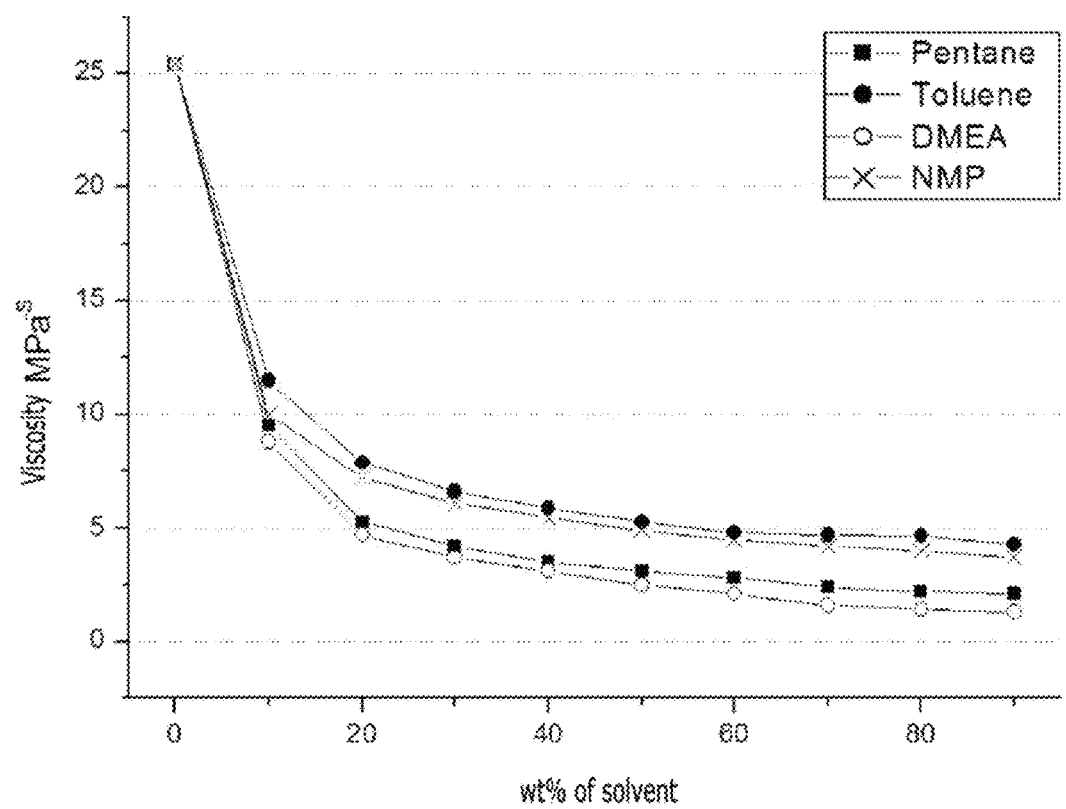
FIG. 4 illustrates a graph showing that viscosity properties of film-forming compositions vary depending on solvents.

As shown in FIG. 4, viscosity of the film-forming composition became higher as the amount of the solvent was increased. In particular, pentane and dimethyethylamine showed excellent improvement of viscosity.

Test for the Improvement Effect on Deposition Properties

Film-forming compositions were prepared using 20 wt % of pentane, DMEA, and N-methylpyrrolidine, respectively. The amount of the solvent, that is 20 wt %, was chosen such that in a comparison with $CpZr(DMA)_3$, the viscosity was improved in the above test. Deposition was performed by using the prepared film-forming compositions as mentioned above. Deposition temperature was 300° C.

Here, Comparative Examples 1 to 4 were obtained using $CpZr(DMA)_3$ alone, $Cp(CH_2)_3NMeZr(NMe_2)_2$ alone, $Cp(CH_2)_3NMeZr(NMe_2)_2$ diluted with 20 wt % of pentane, and $Cp(CH_2)_3NMeZr(NMe_2)_2$ diluted with 20 wt % of N-methylpyrrolidine, respectively. Example used $Cp(CH_2)_3NMeZr(NMe_2)_2$ diluted with 20 wt % of DMEA. The results are shown in FIG. 5.

Figure 5:
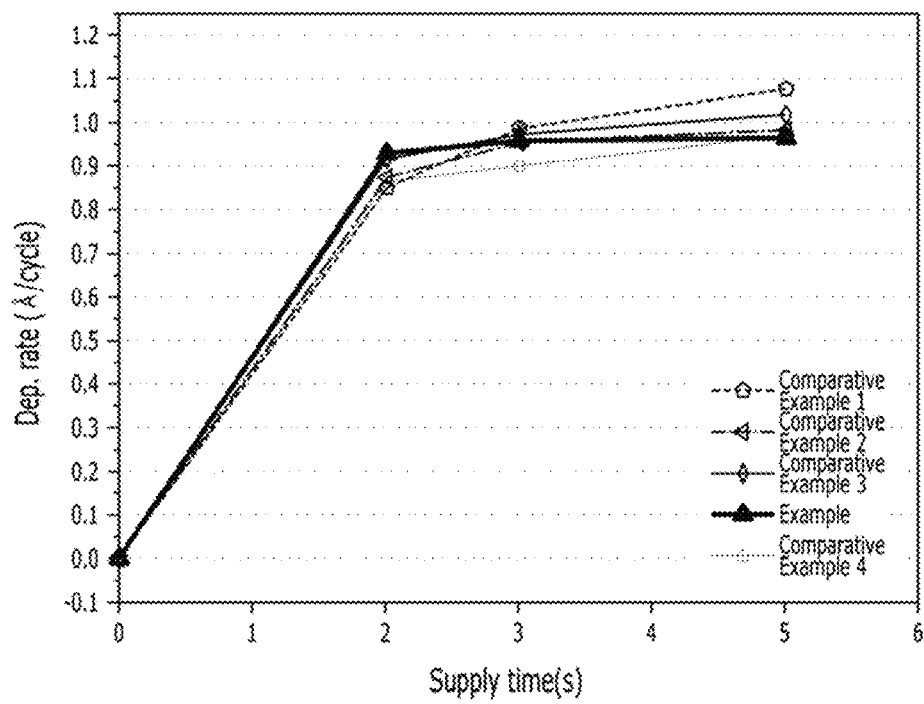
FIG. 5 illustrates a graph showing that deposition properties of film-forming compositions vary depending on solvents.

As shown in FIG. 5, Example and Comparative Examples 1 to 4 were deposited after 2 seconds of feeding of the respective compositions. The deposition rates of the respective compositions were different from one another. For example, in case of Comparative Examples 1 and 2, as the supply time was increased, the deposition rate was increased. In detail, as the supply time was increased, the deposition rate was slightly increased. It may be referred to as "weak tendency for CVD". In contrary, in case of Example and Comparative Examples 3 and 4, although the supply time additionally extends up to 2 or more seconds in addition to the initial 2-second supply, the deposition rate changed insignificantly. In detail, it is shown that in case of Example and Comparative Examples 3 and 4, the CVD reaction was suppressed after the initial 2 seconds of feeding. Specifically, in case of Example, there was substantially no change in deposition rate in comparison with Comparative Examples 3 and 4. Thus, according to Example, it was further improved to suppress the CVD reaction. As such, in case of Example, since the CVD reaction was suppressed, a uniform deposition rate was achieved by the ALD reaction even though the supply time extends. As a result, according to Example, step coverage was remarkably enhanced in comparison with Comparative Examples.

Additionally, the deposition rate was tested depending on DMEA content. Deposition temperature was 300° C. and supply time was 3 seconds. The results are shown in Table 1 and FIG. 6.

TABLE 1

| DMEA content (wt %) | deposition rate(Å/cycle) |
|---|---|
| 10 wt % | 0.94 |
| 15 wt % | 0.935 |
| 20 wt % | 0.93 |
| 30 wt % | 0.925 |
| 50 wt % | 0.92 |
| 60 wt % | 0.915 |
| 70 wt % | 0.91 |
| 90 wt % | 0.91 |

Figure 6:
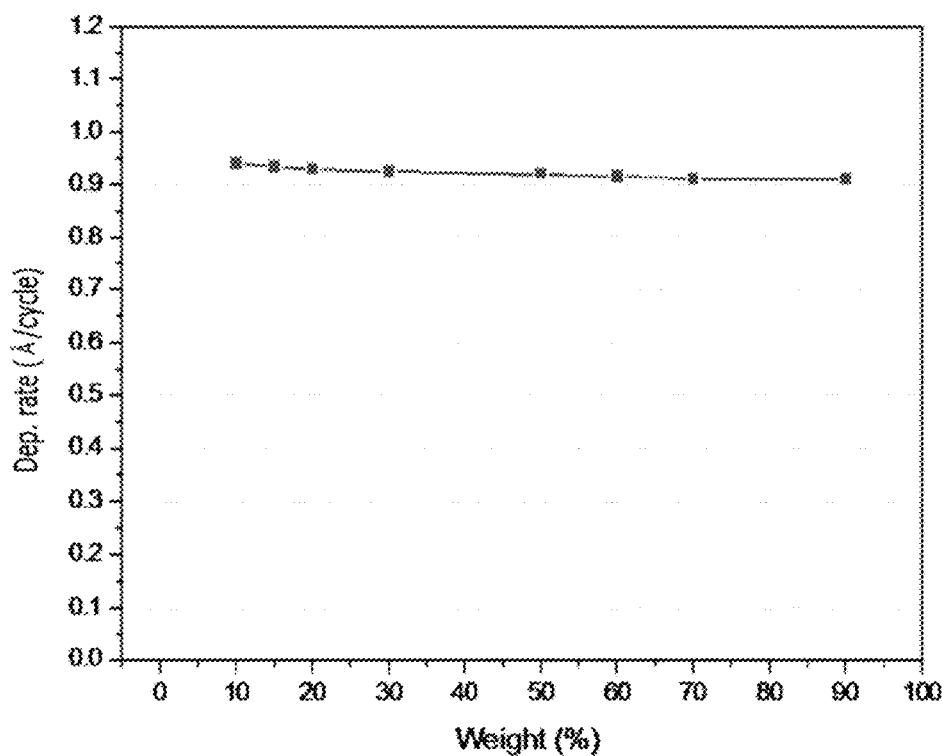
FIG. 6 illustrates a graph showing that deposition rates of film-forming compositions vary depending on the amount of dimethylethylamine.

As shown in Table 1 and FIG. 6, the deposition rate was not meaningfully changed although the solvent content was changed. In view of the results, it is found that the solvent content is preferably 10 to 90 wt % to maintain the deposition rate, improve the viscosity properties and suppress the proneness to CVD.

Test for the Improvement Effect on Step Coverage Properties

In view of the above results, it was expected that viscosity and vapor pressure would be improved through dilution with solvents and thus the film-forming composition would be uniformly delivered inside the trench to improve step coverage properties. After the film-forming composition diluted with solvents was prepared and deposited on a wafer having a trench, the wafer was compared with wafers on which the film-forming compositions containing $CpZr(DMA)_3$ and $Cp(CH_2)_3NMeZr(NMe_2)_2$ were deposited, respectively.

Figure 7:
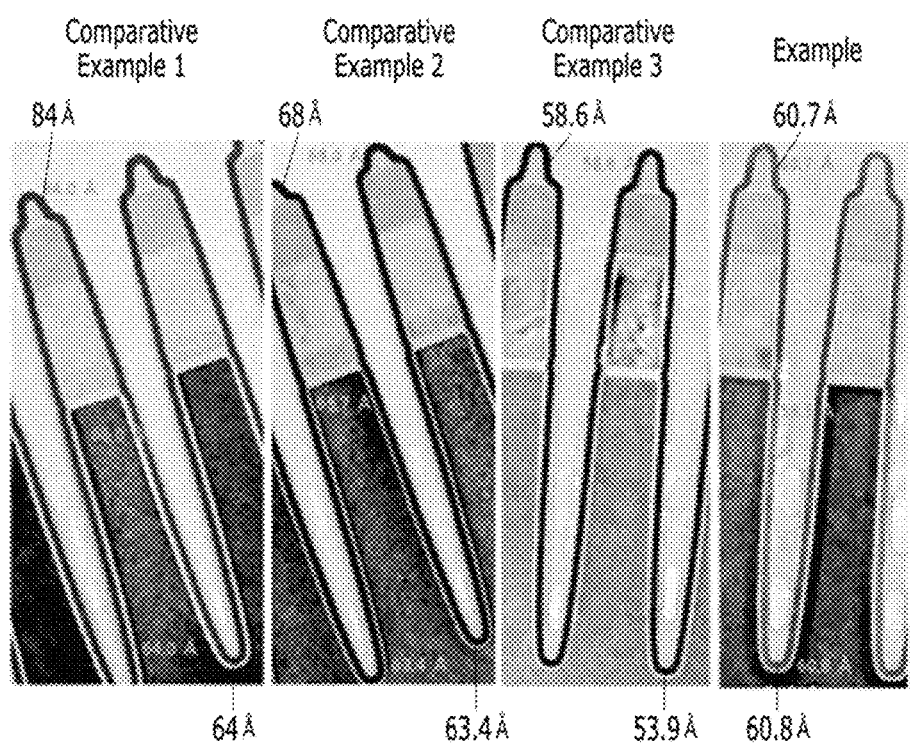
FIG. 7 illustrates a graph showing step coverage properties of film-forming compositions.

As mentioned above, 20 wt % of pentane and DMEA respectively were mixed with $Cp(CH_2)_3NMeZr(NMe_2)_2$ to prepare the Comparative Example 3 and the Example, respectively. Then the film-forming compositions were deposited on the wafer having the trench and the improvement effect on step coverage properties was tested. The results are shown in Table 2 and FIG. 7. The step coverage is a ratio of thickness of a film at bottom of the trench to thickness of the film at top of the trench.

$Cp(CH_2)_3NMeZr(NMe_2)_2$ was diluted with DMEA, had the step coverage of substantially 100%.

Test for the Improvement Effect on Purity in the Deposited Film

DMEA has higher volatility than that of $Cp(CH_2)_3NMeZr(NMe_2)_2$. Accordingly, DMEA is not likely to remain as impurities after deposition. Rather, DMEA may remove impurities due to its high volatility. For supporting this point, element analysis was performed for the deposited films using Auger Electron Spectroscopy (AES). The results are shown in Table 3 and FIG. 8.

TABLE 3

| | Carbon (%) | Nitrogen (%) |
|---|---|---|
| Comparative Example 1 ($CpZr(DMA)_3$) | 0.5 | 0.67 |
| Comparative Example 2 ($Cp(CH_2)_3NMeZr(NMe_2)_2$) | 0.83 | 1.26 |
| Example ($Cp(CH_2)_3NMeZr(NMe_2)_2$ + DMEA) | 0.4 | 0.5 |

Figure 8:
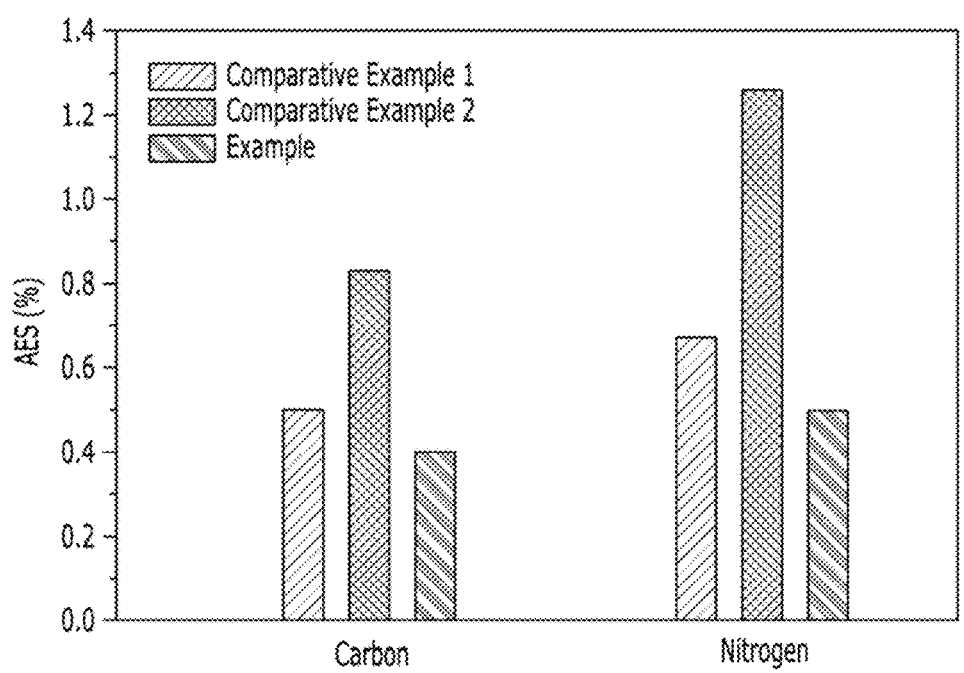
FIG. 8 illustrates a graph showing a change in performance depending on purity of the deposited film.

As shown in Table 3 and FIG. 8, carbon content and nitrogen content of Example ($Cp(CH_2)_3NMeZr(NMe_2)_2$+DMEA) were lower than those of Comparative Example 1 ($CpZr(DMA)_3$) and Comparative Example 2 ($Cp(CH_2)_3NMeZr(NMe_2)_2$). Here, carbon and nitrogen were impurity sources and carbon causes leak current. In particular, carbon content of Example ($Cp(CH_2)_3NMeZr(NMe_2)_2$+DMEA) was lower than that of Comparative Example 1 ($CpZr(DMA)_3$). Accordingly, it is found that DMEA could effectively remove impurities after deposition.

In case of deposition using $Cp(CH_2)_3NMeZr(NMe_2)_2$ having high viscosity, the thickness distribution of the film may be wide. Solvent dilution may overcome this drawback. Most of the solvents showed an improved effect on viscosity and suppression of CVD. However, significant improvement was observed in DMEA. That is, DMEA, particularly used in an amount of 10 to 90 wt %, showed a unique and remarkable improvement effect such as, improvement on viscosity, suppression of proneness to CVD while maintaining deposition rate, excellent step coverage properties and removal of impurities. Such improvement effect was not shown from other solvents.

This is attributed to the steric hindrance of the tertiary amine. The tertiary amine shares non-covalent electron pairs with zirconium. The non-covalent electron pairs improve thermal stability and step coverage. DMEA exists in liquid phase at 25° C. and at 760 Torr, and is a tertiary amine

TABLE 2

| | Comparative Example 1 ($CpZr(DMA)_3$) | Comparative Example 2 ($Cp(CH_2)_3NMeZr(NMe_2)_2$) | Comparative Example 3 ($Cp(CH_2)_3NMeZr(NMe_2)_2$ + pentane) | Example ($Cp(CH_2)_3NMeZr(NMe_2)_2$ + DMEA) |
|---|---|---|---|---|
| Top thickness | 84 Å | 68 Å | 58.6 Å | 60.7 Å |
| Bottom thickness | 64 Å | 63.4 Å | 53.9 Å | 60.8 Å |
| Step coverage | 76.2% | 93.2% | 92% | 100% |

The step coverage was 77% for $CpZr(DMA)_3$ and 93.2% for $Cp(CH_2)_3NMeZr(NMe_2)_2$, respectively. Meanwhile, Comparative Example 3, where $Cp(CH_2)_3NMeZr(NMe_2)_2$ was diluted with pentane, had the step coverage of 92% so that the step coverage properties were not significantly improved compared with the Comparative Example 2 in which no solvent is used. In contrast, Example, where having the lowest steric hindrance. This is why DMEA may show the special improvement effect. In case of a similar experiment using triethylamine (TEA), the improvement effect on step coverage was lower than that of DMEA, and carbon and nitrogen pollution sources were slightly increased due to a relatively high boiling point and steric hindrance.

In accordance with embodiments of the present invention, as a 3-intracyclic Cp-based precursor is stabilized with tertiary amine, excellent thermal stability of the precursor may be maintained while viscosity and volatility of a film-forming composition may be improved due to low viscosity and high volatility of the solvent.

In accordance with the embodiments of the present invention, as a film-forming composition including a 3-intracyclic Cp-based precursor stabilized with tertiary amine is used, adsorption efficiency and stability of the precursor may be increased and process time may be reduced. Consequently, films with the improved uniformity and step coverage properties may be formed.

While the present invention has been described with respect to the specific embodiments, it will be apparent to those skilled in the art that various changes and modifications may be made without departing from the spirit and scope of the invention as defined in the following claims.

What is claimed is:

1. A film-forming composition comprising:
   a 3-intracyclic cyclopentadienyl precursor and dimethyethylamine,
   wherein the 3-intracyclic cyclopentadienyl precursor is represented by the following formula 1,

[Formula 1]

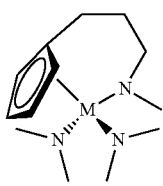

wherein M is selected from the group consisting of Zr, Hf, and Ti.

2. The film-forming composition of claim 1, wherein the dimethyethylamine is included in the composition in an amount of 1 to 99 wt % based on the total amount of the composition.

3. The film-forming composition of claim 1, wherein the precursor and the dimethyethylamine have a weight ratio of 1:99 to 99:1.

4. A method for fabricating a film comprising:
   depositing a film-forming composition over a substrate to form a film,
   wherein the film-forming composition comprises a 3-intracyclic cyclopentadienyl precursor and dimethyethylamine,
   wherein the 3-intracyclic cyclopentadienyl precursor is represented by the following formula 1,

[Formula 1]

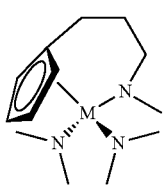

wherein M is selected from the group consisting of Zr, Hf, and Ti.

5. The method of claim 4, wherein the film is deposited by Atomic Layer Deposition.

6. The method of claim 5, wherein the depositing of the film includes:
   preparing a liquid-phase composition by dissolving the precursor in the dimethyethylamine,
   placing a substrate in a chamber, and
   introducing the liquid-phase composition into the chamber through Liquid Delivery System.

7. The method of claim 6, wherein the depositing of the film further includes vaporizing the liquid-phase composition, and
   wherein the introducing of the liquid-phase composition includes introducing the vaporized liquid-phase composition into the chamber.

8. The method of claim 4, wherein the dimethyethylamine is included in an amount of 1 to 99 wt % based on the total amount of the film-forming composition.

9. The method of claim 4, wherein the precursor and the dimethyethylamine has a weight ratio of 1:99 to 99:1.

10. A method for fabricating a film comprising:
    preparing a liquid-phase metal precursor by dissolving a 3-intracyclic cyclopentadienyl metal precursor in dimethyethylamine, wherein the 3-intracyclic cyclopentadienyl metal precursor is represented by the following formula 1,

[Formula 1]

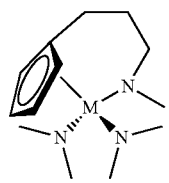

wherein M is selected from the group consisting of Zr, Hf, and Ti;
    vaporizing the liquid-phase metal precursor and introducing the vaporized metal precursor into a chamber with a substrate;
    adsorbing the vaporized metal precursor over the substrate; and
    feeding a reactant reactable with the adsorbed metal precursor to form a metal-containing film over the substrate.

11. The method of claim 10, wherein the metal-containing film comprises a metal selected from the group consisting of Zr, Ti, Hf, an oxide of the metal, and a nitride of the metal.

12. The method of claim 10,
    wherein the forming of the metal-containing film is performed by atomic layer deposition or chemical vapor deposition.

* * * * *